(12) United States Patent
Ptchelintsev et al.

(10) Patent No.: US 7,592,024 B1
(45) Date of Patent: Sep. 22, 2009

(54) **TOPICAL COMPOSITIONS CONTAINING *MELICOPE HAYSELII* AND A METHOD OF TREATING SKIN**

(75) Inventors: Dmitri S. Ptchelintsev, Jersey City, NJ (US); Laurence Dryer, Port Jefferson, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 12/344,787

(22) Filed: Dec. 29, 2008

(51) Int. Cl.
*A61K 36/00* (2006.01)
(52) U.S. Cl. ....................... 424/725; 424/401
(58) Field of Classification Search ........................ None
See application file for complete search history.

(56) References Cited

OTHER PUBLICATIONS

Brophy (J. Essent. Oil Res. (2004), vol. 16, pp. 286-293).*
http://www.merriam-webster.com/dictionary/lotion— accessed May 2009.*
Thornfeldt, CR (2008) J. Cosmet. Dermatol. 7:78-82.
Bissett, et al. (1990) Photodermatol. Photoimmunol. Photomed. 7:153-8.
Bekersky et al, 2001, J. Am. Acad. Dermatol. 441:S17-S27.
Furue, et al. (2006) Dermatol. Ther. 19:118-26.

* cited by examiner

*Primary Examiner*—Susan C Hoffman
(74) *Attorney, Agent, or Firm*—Charles J. Zeller; Joan M. McGillycuddy; Anthony M. Santini

(57) ABSTRACT

Cosmetic compositions comprising an extract of *Melicope hayesii* and methods of using such compositions to impart anti-aging benefits to the skin are disclosed. These compositions are believed to have modulatory activity against at least one biochemical pathway implicated in skin aging.

23 Claims, No Drawings

TOPICAL COMPOSITIONS CONTAINING *MELICOPE HAYSELII* AND A METHOD OF TREATING SKIN

FIELD OF INVENTION

The present invention relates generally to topical compositions for topical application to the skin which comprise *Melicope hayesii* extracts and the use of such compositions to provide benefits to the skin.

BACKGROUND OF THE INVENTION

The gradual development of facial wrinkles, whether fine surface lines or deeper creases and folds, is an early sign of accumulated skin damage and skin aging, which may be intrinsic and/or caused or accelerated by external factors. For example, premature aging and wrinkling of the skin may be accelerated by excessive exposure to the sun and other damaging elements, overactive facial expression muscles, frequent use of tobacco products, poor nutrition, or skin disorders. Fine surface wrinkles that progress to deeper creases, deepening facial expression due to repeated skin folding, and deep folds which develop with one's maturity are visible changes which may combine to portray a less desirable appearance. Several invasive techniques are available in which substances are injected or implanted in the area of the skin which either temporarily weaken the muscles or act as skin volume fillers. However, invasive techniques are often risky and require the supervision or assistance of a physician, which can be inconvenient and costly, and non-invasive treatments have historically met with only minimal success. Regardless of the cause of facial creases or folds, safe and effective treatments for reduction or elimination of these problems have been exceedingly difficult to achieve.

Thornfeldt et al. recommended that skin care regimens using active ingredients that are recommended by physicians who treat mucocutaneous conditions including aging should become more focused on reversing and preventing chronic inflammation. Thornfeldt reported that chronic inflammation appears strongly linked to many preventable and treatable skin diseases and conditions such as visible skin aging. Thornfeldt stated that mucocutaneous inflammation as the final common pathway of many systemic and mucocutaneous diseases including extrinsic aging has been established at the molecular and cellular levels. (see Thornfeldt, C R (2008) *J. Cosmet. Dermatol.* 7:78-82).

Bissett et al. reported that albino hairless mice exposed chronically to suberythemal doses of ultraviolet (UV) radiation displayed an increase in dermal cellularity, including inflammatory cells. In one experiment, Bissett observed that topical hydrocortisone, ibuprofen, and naproxen protected against UVB radiation-induced visible wrinkling, tumor formation, and histological alternations in albino hairless mice. In another experiment, Bissett observed that hydrocortisone and naproxen were effective against UVA radiation-induced visible skin sagging and histological alterations in albino hairless mice. The investigators hypothesized that this data suggested role for inflammation in chronic photodamage. (see Bissett, et al. (1990) *Photodermatol. Photoimmunol. Photomed.* 7:153-8).

Calcineurin is a protein phosphatase involved in the activation of Nuclear factor of activated T cells ("NFAT"), a transcription factor. Activation of NFAT transcription factor stimulates T cells involved in calcium trafficking and inflammatory responses. Expression of calcineurin in skin increases intrinsically over time with age.

Topical calcineurin inhibitors, such as a tacrolimus ointment commercially available as PROTOPIC®, have been used to treat atopic dermatitis, which is an eczematous skin disease that has typically been treated with topical steroids. A tacrolimus ointment has been reported to inhibit calcineurin, which results in suppression of antigen-specific T-cell activation and inhibition of inflammatory cytokine release. (see, e.g., Bekersky et al, 2001, *J. Am. Acad. Dermatol.* 441:S17-S27). Furue et al. reported that tacrolimus ointment was used as a first-line treatment for the inflammation of atopic dermatitis. (see e.g. Furue, et al. (2006) *Dermatol. Ther.* 19:118-26). Another commercially available calcineurin inhibitor is pimecrolimus, which is commercially available in a cream as ELIDEL®.

*Melicope hayesii* is a shrub in the *Melicope* genus and the Rutaceae family that may be found in the wild on the north coast of New South Wales (NSW), Australia. The *Melicope* plant genus includes about 150 different species of shrubs and trees in the family, which may be found in western Hawaii, tropical regions of Asia, Australia and New Zealand. Plants in the *Melicope* genus are commonly referred to as "Corkwood" or "Doughwood" in Australia and as "Alani" in Hawaii.

There remains a need for cosmetic compositions which reduce signs of aging. It is therefore an object of the invention to provide new compositions and methods for inhibiting calcineurin activity. It is a further object of the invention to improve the overall appearance of skin, including treating, reversing, and/or preventing signs of aging, such as skin wrinkles, by inhibiting calcineurin activity with new cosmetic compositions.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that extracts of *Melicope hayesii* are capable of inhibiting calcineurin activity and thus are beneficial agents against various signs of intrinsic aging and photo-aging of skin.

In one aspect of the invention, cosmetic compositions are provided for imparting an anti-aging benefit to human skin comprising an amount of an extract of *Melicope hayesii* effective to provide an anti-aging benefit to the skin, and a cosmetically acceptable vehicle. The topical composition may be in the form of a lotion, cream, gel or foam.

In another aspect of the invention, cosmetic compositions are provided for topical application. The cosmetic compositions for topical application which comprises an effective amount of an extract of *Melicope hayesii* to treat, reverse, ameliorate and/or prevent signs of skin damage or skin aging. Such benefits include without limitation, the following:
 (a) treatment, reduction, and/or prevention of fine lines or wrinkles,
 (b) reduction of skin pore size,
 (c) improvement in skin thickness, plumpness, and/or tautness;
 (d) improvement in skin suppleness and/or softness;
 (e) improvement in skin tone, radiance, and/or clarity;
 (f) improvement in procollagen and/or collagen production;
 (g) improvement in maintenance and remodeling of elastin;

(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization and/or hydration;
(o) increase in and/or preventing loss of skin elasticity and/or resiliency;
(p) treatment, reduction, and/or prevention of skin sagging; and/or
(q) treatment, reduction, and/or prevention of discoloration of skin.

Also provided is a method of imparting an anti-aging benefit to skin comprising topically applying to skin in need thereof a composition in a cosmetically acceptable vehicle comprising an extract of *Melicope hayesii* and a cosmetically acceptable vehicle. The extract may be present in an amount sufficient to inhibit calcineurin activity.

In another aspect of the invention, a method of treating wrinkles and/or fine lines on skin is provided, comprising topically applying to the wrinkle an/or fine lines on the skin in need thereof a composition comprising an effective amount of an extract of *Melicope hayesii* in a cosmetically acceptable vehicle for a time sufficient to reduce the severity of the wrinkles or fine lines.

These and other aspects of the invention will be better understood by reference to the following detailed description of the invention.

DETAILED DESCRIPTION

All terms used herein are intended to have their ordinary meaning unless otherwise provided.

In the following description of the invention, it is to be understood that the terms used herein have their ordinary and accustomed meanings in the art, unless otherwise specified. All weights percentages referred to herein are given in terms of "% by weight" or "% wt" of the total composition, which refers to the weight percent of the total formulation after addition of any carriers, solvents, emollients, or other components before application to the skin, unless otherwise indicated.

It has surprisingly been found that an extract of *Melicope hayesii* is capable of inhibiting calcineurin activity. Expression of calcineurin in skin increases intrinsically over time with age. Calcineurin is believed to be related to inflammation, which may have a deleterious effect on the appearance of skin. Specifically, inflammation (including acne, eczema, contact allergies) is believed to cause the breakdown of collagen, create pigmentary irregularities (splotchyness), and cause scarring. Inhibition of calcineurin is expected to provide a decrease in the inflammation contribution to skin aging. In view of these findings and others, a topical composition comprising an extract of *Melicope hayesii* is contemplated to be useful in combating signs of skin damage and skin aging, including reducing fine lines and wrinkles, skin sagging or atrophy, loss of elasticity, discoloration of skin, and related signs of aging in skin through inhibition of calcineurin activity.

The term "wrinkle" or "wrinkling" refers to both fine wrinkling and coarse wrinkling. Fine wrinkling or fine lines refers to superficial lines and wrinkles on the skin surface. Coarse wrinkling refers to deep furrows, particularly deep lines/wrinkles on the face and around the eyes, including of expression lines such as frown lines and wrinkles, forehead lines and wrinkles, crow's feet lines and wrinkles, nasolabial fold and marionette lines and wrinkles. Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth. Wrinkles can be assessed for number, length, and depth of the lines.

Discoloration of skin includes discrete pigmentation, which is commonly known as pigment spots or "age spots," and mottled pigmentation. Discrete pigmentation are distinct uniform areas of darker pigment and may appear as brown spots or freckles on the skin. Mottled pigmentation are dark blotches that are larger and more irregular in size and shape than discrete pigmentation. Areas of mottled pigmentation tend to become darker with sun exposure.

Elasticity of the skin refers to the springiness and resilience of skin's ability to regain its original shape and size after deformation. Elasticity of the skin may be evaluated by a pinch test that can either cause deformation by stretching or squeezing the skin.

The present invention provides compositions for topical application which comprises an effective amount of an extract of *Melicope hayesii* to treat, reverse, ameliorate and/or prevent signs of skin damage or skin aging. Such benefits include without limitation, the following:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization and/or hydration;
(o) increase in and/or preventing loss of skin elasticity and/or resiliency;
(p) treatment, reduction, and/or prevention of skin sagging; and/or
(q) treatment, reduction, and/or prevention of discoloration of skin.

In practice, the compositions of the invention are applied to skin in need of treatment. That is, skin which suffers from a deficiency or loss in any of the foregoing attributes or which would otherwise benefit from improvement in any of the foregoing skin attributes.

In certain preferred embodiments the compositions and methods of the invention are directed to the prevention, treatment, and/or amelioration of fine lines and/or wrinkles in the skin. In this case, the compositions are applied to skin in need of treatment, by which is meant skin having wrinkles and/or fine lines. Preferably, the compositions are applied directly to the fine lines and/or wrinkles. The compositions and methods are suitable for treating fine lines and/or wrinkles on any surface of the skin, including without limitation, the skin of the face, neck, and/or hands.

One component of the invention is a botanical component derived from the *Melicope hayesii* plant. For use in the compositions of this invention, the botanical component is preferably derived directly from the *Melicope hayesii* plants. The botanical component may be in a pure form, a semi-pure form, or unpurified form. The *Melicope hayesii* botanical component may be in the form of a liquid, a semi-solid or a solid consistency. Preferably, the botanical component is an essential oil.

Specifically, the botanical component is derived from raw materials collected from the *Melicope hayesii* plants, which may contain the desired constituent(s), such as seeds, needles, leaves, roots, bark, cones, stems, rhizomes, callus cells, protoplasts, organs and organ systems, and meristems. Preferably, the raw materials are collected from the leaves and terminal branchlets of the *Melicope hayesii* plants. In certain embodiments, the raw materials collected from the *Melicope hayesii* plants are ground to small particle sizes. In addition, the raw materials may be dried to reduce water content. The raw materials may be dried by a number of different means, such as, for example, air-dried, oven-dried, rotary evaporated under vacuum or lyophilized.

The extract of *Melicope hayesii* may be obtained by distilling the raw materials with a stripping agent. The stripping agent may be a liquid that is miscible, immiscible, or partially miscible with the desired extract from *Melicope hayesii*. Suitable stripping agents include, but are not limited to, water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. In one embodiment, the stripping agent is immiscible with the desired extract (e.g., essential oil) from *Melicope hayesii*. Preferably, the stripping agent is water. More preferably, the *Melicope hayesii* extract is obtained by steam distillation. The *Melicope hayesii* extract (e.g., essential oil) may be collected by phase separation from the stripping agent. It is believed that the stripping agent increases the overall vapor pressure of a distillation system for obtaining an extract of *Melicope hayesii* and thereby reducing the boiling point of the desired product, the *Melicope hayesii* extract (or specifically, the *Melicope hayesii* essential oil).

In other embodiments, *Melicope hayesii* botanical component may be in the form of an extract obtained by solvent extraction, preferably obtained by an organic solvent extraction. Briefly, the organic solvent extraction method involves washing and extracting the raw materials, which may be whole or ground into small particle sizes, using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field. The raw materials are pushed in the extracting machine by a thruster, which slowly moves the plant raw materials forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the *Melicope hayesii* plant constituents is used, typically between about 1-10 hours is suitable, and more preferably is between about 2-8 hours, and most preferably is between about 3-6 hours. The temperature of extraction is between about 30° C.-100° C., preferably between about 40° C.-70° C., and more preferably between about 50° C.-60° C. The collected extract is then fine-filtered to remove debris, and may be used directly, or is concentrated, for example by distilling the solvent or by other conventional processing. The solution of extract actives may be rotary evaporated under vacuum or lyophilized. A typical extract actives content is above about 25%, preferably above 50%, and the extract can also be provided an essential oil or a concentrate having a semi-solid or solid consistency.

Similarly, aqueous-organic solvent extraction involves initially collecting raw materials from the *Melicope hayesii* plants, which may be whole or ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly as an essential oil or a concentrate, or dried by a number of different means, such as, for example, air-dried, oven-dried, rotary evaporated under vacuum or lyophilized to a semi-solid or solid consistency.

It should also be noted that different plants containing different constituents can be mixed and extracted together with *Melicope hayesii*. This process of mixed extraction can preferably be used for extracting those plants containing constituents with similar solubility as *Melicope hayesii* in the solvent used for extraction, such as ethanol. The mixture of extracts can be concentrated and stored in an appropriate solvent.

In another embodiment, the *Melicope hayesii* extract as used herein, also includes "synthetic" extracts, i.e., various combinations of known *Melicope hayesii* plant components and/or constituents that are combined to substantially mimic the composition and/or activity of a *Melicope hayesii* plant extract of natural origin. Preferably, the synthetic extracts have substantially the same number of active components as a natural *Melicope hayesii* plant material. The correspondence of the numerical incidence of actives between the synthetic extracts and the natural *Melicope hayesii* plant material may also be described in terms of "percent commonality." The synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract.

The compositions according to the invention can be formulated in a variety of forms for topical application and will comprise from about 0.0001% to about 90% by weight of an extract of *Melicope hayesii*, and preferably will comprise from about 0.001% to about 25% by weight, and more preferably from about 0.01% to about 10% by weight. Within the more preferred range, the composition may comprise a *Melicope hayesii* extract within a range from about 0.1%, 0.25%, 0.5%, 0.75% or 1% up to 5%, 7.5% or 10% by weight of the total composition. The compositions will comprise an effective amount of an extract of *Melicope hayesii*, by which is meant an amount sufficient to inhibit calcineurin activity in given area of skin when topically applied thereto. The above amounts refer to an "active amount" of a *Melicope hayesii* extract. The term "active amount" refers to the amount of *Melicope hayesii* extract, absent diluent, solvent, carrier, filler or any other ingredient. An "amount effective" or an "effective amount" to provide a particular anti-aging benefit to the skin refers to the "active amount" of extract required to provide a clinically measurable improvement in the particular manifestation of skin aging when applied for a time sufficient to provide a clinically measurable improvement in the particular manifestation of skin aging.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The compositions can include a cosmetically acceptable vehicle. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion preferably has one or more organic compounds, including emollients; humectants (such as butylene glycol, propylene glycol, Methyl gluceth-20, and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers included emulsifying waxes, emulsifying polyhydric alcohols, polyether polyols, polyethers, mono- or di-ester of polyols, ethylene glycol monostearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. The preferred emulsifiers include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: $C_{10-30}$ alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11 th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, from about 0.1% to about 3% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising —(EO)$_m$— and/or —(PO)$_n$— groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

The compositions may include liposomes. The liposomes may comprise other additives or substances and/or may be modified to more specifically reach or remain at a site following administration.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives (e.g., DMDM Hydantoin/Iodopropynylbutylcarbonate), stabilizers, pharmaceutical agents, photostabilizing agents, neutralizers (e.g., triethanolamine) and mixtures thereof. In addition to the foregoing, the cosmetic compositions of the invention may contain any other compound for the treatment of skin disorders.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions may include additional skin actives such as, but are not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Anogeissus latifolia, Asmunda japonica, Azadirachta indica, Butea frondosa, Butea monosperma, Cedrus deodara, Emblica officinalis, Ficus benghalensis, Glycyrrhiza glabra, Ilex purpurea* Hassk, *Inula racemosa, Ligusticum chuangxiong, Ligusticum lucidum, Mallotus philippinensis, Mimusops elengi, Morinda citrifolia, Moringa oleifera, Naringi crenulata, Nerium indicum, Psoralea corylifolia, Stenoloma chusana, Terminalia bellerica*, tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, cetyl ethylhexanoate, $C_{12-15}$ alkyl benzoate, isopropyl isostearate, diisopropyl dimer dillinoeate, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

It is preferred that the composition be essentially free of components having a strong oxidizing potential, including for example, organic or inorganic peroxides. By "essentially free of" these components is meant that the amounts present are insufficient to have a measurable impact on the calcineurin inhibiting activity of an extract of *Melicope hayesii*. In some embodiments, this will be, in relation to the amount of *Melicope hayesii*, less than 1% by weight.

In one embodiment, the composition of the invention comprising an extract of *Melicope hayesii* may have a pH between about 1 and about 8. In certain embodiments, the pH of the composition will be acidic, i.e., less than 7.0, and preferably will be between about 2 and about 7, more preferably between about 3.5 and about 5.5.

The invention provides a method for treating aging skin by topically applying a composition comprising an extract of *Melicope hayesii*, preferably in a cosmetically acceptable vehicle, over the affected area for a period of time sufficient to reduce, ameliorate, reverse or prevent dermatological signs of aging. This method is particularly useful for treating signs of skin photoaging and intrinsic aging.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

Without wishing to be bound by any particular theory, it is believed that the compositions of the present invention enhance and improve the aesthetic appearance of skin by reducing inflammation and/or by inhibiting calcineurin activity in skin fibroblast cells.

The composition will typically be applied to the skin one, two, or three times daily for as long as is necessary to achieve desired anti-aging results. The treatment regiment may comprise daily application for at least one week, at least two weeks, at least four weeks, at least eight weeks, or at least twelve weeks. Chronic treatment regimens are also contemplated.

A composition comprising an extract of *Melicope hayesii* is topically applied to an "individual in need thereof," by which is meant an individual that stands to benefits from reducing visible signs of skin damage or aging. In a specific embodiment, the *Melicope hayesii* extract is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive compositions comprising a *Melicope hayesii* extract to the skin of an individual in need thereof, e.g., topically application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles on the skin of the hands, arms, legs, neck, chest, and face, including the forehead.

It is also contemplated that the compositions of the invention will be useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in patients that have not manifested signs of skin aging, most commonly in individuals under 25 years of age. The method may also reverse or treat signs of aging once manifested as is common in patients over 25 years of age.

EXAMPLES

Example 1

Preparation of *Melicope hayesii* Extract

The process generally follows a combination of steam distillation and hydro-distillation, as it uses partial immersion of the biomass and boiling water steam, although it is typically referred to as steam distillation. Steam distillation relies on heat to open the oil glands in the plant and the essential oil and water to mix. Then the increase in vapor pressure and corresponding reduction in boiling point which occurs with the mixing of 2 immiscible liquids allows the essential oil, which would normally have a boiling point of greater than 200° C., to boil at less than 100° C.

Leaves and terminal branchlets were cut from stands of *Melicope hayesii* growing wild on the north coast of New South Wales (NSW), Australia. Approximately 2.102 Kg of leaf biomass was loaded loosely into a 20 Liter reaction vessel set up as a distillation unit with receiver condenser and 500 ml separating flask. 4 Liters of Hot Water were added to the vessel and additional heat added via a hot plate. The flow rate of the condenser water was adjusted to give a distillate temperature of at least 50° C. in the separating funnel. The essential oil floated on the water. At approximately 1 hour intervals the water was drained off and returned to the vessel. The distillation was stopped after 8.5 hours when no further oil was distilled. The water in the separating flask was drained and the essential oil tapped off. The 2.102 Kg of leaf biomass produced 3.35 g of essential oil, a yield of 0.16%. The essential oil was found to have a relative density at 20° C. of 0.950 and a Refractive Index of 1.510 at 20° C.

As noted in the remaining specification, modifications and adaptations of this extraction process are possible, particularly during a scale-up to larger volumes for production.

Example 2

Inhibition of Calcineurin Activity

An ex-vivo phosphatase assay was used to evaluate the ability of a *Melicope hayesii* extract to modulate calcineurin activity.

Ex-vivo phosphatase assay: The modulation of calcineurin activity is monitored using a DiFMUP (6,8-difluoro-7-hydroxy-4-methylcoumarin phosphate) phosphatase assay (see, e.g., Wegner et al., 2007, Methods Mol. Biol. 365:61-69, hereby incorporated by reference in its entirety). Dephosphorylation of DiFMUP leads to the formation of a highly fluorescent and stable product: Di4MU. Varying concentrations of the extract are added to a reaction buffer, typically consisting of 50 mM Tris-HCl, pH 7.4, 0.0125% Bovine Serum Albumin (BSA), 0.1 mM CaCl, 400 U/ml calmodulin and 1 mM NiCl. The reaction buffer mixture is incubated at 37° C. for 30 min. DiFMU substrate is then added to a concentration of 10 µM, and the mixture returned to 37° C. incubation for a further 15 min. Fluorescence intensity is determined on a Spectrofluorometer.

Results: At the lowest concentration tested, a *Melicope hayesii* extract was found to inhibit calcineurin activity by 17% at a concentration of 0.001% weight/volume. Increasing *Melicope hayesii* extract concentration resulted in a dose dependent inhibition of calcineurin activity, decreasing activity by 69% and 97% at 0.01% and 0.1% concentration, respectively. The $IC_{50}$ of the compound was estimated as 0.0047%. The results suggest that topical application of compositions comprising a *Melicope hayesii* extract will result in improvements of symptoms associated with inflammatory skin conditions.

Example 3

Exemplary Compositions

Cosmetic compositions comprising an extract of *Melicope hayesii* for topical application to the skin are provided in Table 1.

TABLE 1

| Components | Composition: Weight % | | | |
|---|---|---|---|---|
| | 1 | 2 | 3 | 4 |
| *Melicope hayesii* extract | 0.3 | 0.03 | 0.01 | 0.005 |
| Acrylates/$C_{10-30}$ Alkyl Acrylate Crosspolymer | 1 | 1 | 1 | 1 |
| Cetyl Ethylhexanoate | 10 | 10 | 10 | 10 |
| $C_{12-15}$ Alkyl Benzoate | 3.9 | 3.9 | 3.9 | 3.9 |
| Isopropyl Isostearate | 3 | 3 | 3 | 3 |
| Diisopropyl dimer dillinoleate | 0.1 | 0.1 | 0.1 | 0.1 |
| Tocopheryl acetate | 0.5 | 0.5 | 0.5 | 0.5 |
| Butylene glycol | 2 | 2 | 2 | 2 |
| Propylene glycol | 1 | 1 | 1 | 1 |
| Dimethicone PEG-7 isostearate | 0.5 | 0.5 | 0.5 | 0.5 |
| Methyl gluceth-20 | 0.5 | 0.5 | 0.5 | 0.5 |
| Triethanolamine | 1 | 1 | 1 | 1 |
| Acrylates/acrylamide copolymer/mineral oil | 1.5 | 1.5 | 1.5 | 1.5 |
| DMDM Hydantoin/Iodopropynyl-butylcarbonate | 0.4 | 0.4 | 0.4 | 0.4 |
| Deionized water | q.s. | q.s. | q.s. | q.s. |
| Total: | 100 | 100 | 100 | 100 |

These compositions are believed to be effective to treat, reverse, ameliorate and/or prevent signs of skin aging, specifically, the compositions are believed to reduce the appearance of fine lines and wrinkles in the skin. The compositions of Table 1 are applied to skin in need of treatment, by which is meant skin in need of an anti-aging benefit, and in particular skin having wrinkles and/or fine lines. The cosmetic compositions may be applied directly to the fine lines and/or wrinkles. The exemplary compositions may be applied to treat, reverse, ameliorate and/or prevent fine lines and/or wrinkles on any surface of the skin, including without limitation, the skin of the face, neck, and/or hands.

The cosmetic compositions are applied to the skin, fine line and/or wrinkle one, two or three times daily for as long as is necessary to achieve desired anti-aging results, which treatment regiment may comprise daily application for at least one week, at least two weeks, at least four weeks, at least eight weeks, or at least twelve weeks. Alternatively, the exemplary cosmetic compositions may be used in chronic treatment of the skin, fine line and/or wrinkle.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for imparting an anti-aging benefit to human skin comprising:
    topically applying to the skin of an individual in need thereof a composition in a cosmetically acceptable vehicle comprising an extract of *Melicope hayesii* in an amount effective to impart the anti-aging benefit to the skin.

2. The method according to claim 1, wherein said extract is present in an amount sufficient to inhibit calcineurin activity.

3. The method according to claim 1, wherein said extract is present in an amount from 0.0001 weight % to 90 weight % based on total weight of the composition.

4. The method according to claim 3, wherein said extract is present in an amount from 0.001 weight % to 25 weight % based on the total weight of the composition.

5. The method according to claim 4, wherein said extract is present in an amount from 0.01 weight % to 10 weight % based on the total weight of the composition.

6. The method according to claim 1, wherein said anti-aging benefit is selected from the group consisting of:
(a) treatment, reduction, and/or prevention of fine lines or wrinkles,
(b) reduction of skin pore size;
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by menopause;
(n) improvement in skin moisturization;
(o) increase in and/or preventing loss of skin elasticity;
(p) treatment, reduction, and/or prevention of skin sagging; or
(q) treatment, reduction, and/or prevention of discoloration of skin.

7. The method according to claim 6, wherein said antiaging benefit is treatment, reduction, and/or prevention of fine lines or wrinkles.

8. The method according to claim 6, wherein said antiaging benefit is treatment, reduction, and/or prevention of skin sagging.

9. The method according to claim 6, wherein said antiaging benefit is treatment, reduction, and/or prevention of discoloration of skin.

10. The method according to claim 6, wherein said antiaging benefit is increase in and/or preventing loss of skin elasticity.

11. The method of claim 1, wherein the extract of *Melicope hayesii* is obtained by steam distillation.

12. A method for treating wrinkles and/or fine lines on skin, comprising:
topically applying to said wrinkle an/or fine lines on the skin of an individual in need thereof a composition comprising an effective amount of an extract of *Melicope hayesii* in a cosmetically acceptable vehicle for a time sufficient to reduce the severity of said wrinkles or fine lines.

13. The method of claim 12, wherein the extract of *Melicope hayesii* is obtained by steam distillation.

14. A topical composition for imparting an anti-aging benefit to skin comprising:
an amount of an extract of *Melicope hayesii* effective to impart an anti-aging benefit to the skin; and
a cosmetically acceptable vehicle;
said topical composition being in the form of a lotion, cream, ointment, gel, or stick.

15. The composition according to claim 14, wherein said extract is present in an amount sufficient to inhibit calcineurin activity.

16. The composition according to claim 14, wherein said extract is present in an amount from 0.0001 weight % to 90 weight % based on total weight of the composition.

17. The composition according to claim 16, wherein said extract is present in an amount from 0.001 weight % to 25 weight % based on the total weight of the composition.

18. The composition according to claim 17, wherein said extract is present in an amount from 0.01 weight % to 10 weight % based on the total weight of the composition.

19. The method of claim 14, wherein the extract of *Melicope hayesii* is obtained by steam distillation.

20. The composition according to claim 14, wherein said cosmetically acceptable vehicle comprises a water-in-oil or oil-in-water emulsion.

21. The composition according to claim 14, wherein the extract is in combination with at least one other skin active.

22. The composition of claim 14, wherein the extract is in combination with at least one other botanical.

23. The composition of claim 22, wherein the other botanical comprises is selected from the group consisting of *Abies pindrow, Acacia catechu, Anogeissus latifolia, Asmunda japonica, Azadirachta indica, Butea frondosa, Butea monosperma, Cedrus deodara, Emblica officinalis, Ficus benghalensis, Glycyrrhiza glabra, Ilex purpurea* Hassk, *Innula racemosa, Ligusticum chiangxiong, Ligusticum lucidum, Mallotus philippinensis, Mimusops elengi, Morinda citrifolia, Moringa oleifera, Naringi crenulata, Nerium indicum, Psoralea corylifolia, Stenoloma chusana, Terminalia bellerica*, tomato glycolipid, and mixtures thereof.

* * * * *